United States Patent
Ziegler et al.

(10) Patent No.: US 7,596,204 B2
(45) Date of Patent: Sep. 29, 2009

(54) METHOD AND DEVICE FOR THE ITERATIVE RECONSTRUCTION OF CARDIAC IMAGES

(75) Inventors: Andy Ziegler, Hamburg (DE); Michael Grass, Buchholz in der Nordheide (DE); Thomas Koehler, Norderstedt (DE)

(73) Assignee: Koninklijke Philips Electronics N.V., Eindhoven (NL)

(*) Notice: Subject to any disclaimer, the term of this patent is extended or adjusted under 35 U.S.C. 154(b) by 65 days.

(21) Appl. No.: 11/908,415

(22) PCT Filed: Mar. 9, 2006

(86) PCT No.: PCT/IB2006/050741

§ 371 (c)(1),
(2), (4) Date: Sep. 12, 2007

(87) PCT Pub. No.: WO2006/097871

PCT Pub. Date: Sep. 21, 2006

(65) Prior Publication Data

US 2008/0253502 A1    Oct. 16, 2008

(30) Foreign Application Priority Data

Mar. 17, 2005    (EP)    ................... 05102096

(51) Int. Cl.
*A61B 6/00*    (2006.01)
(52) U.S. Cl. .............................. 378/8; 378/4
(58) Field of Classification Search ............ 378/4, 378/8
See application file for complete search history.

(56) References Cited

U.S. PATENT DOCUMENTS

| | | | |
|---|---|---|---|
| 5,991,356 A * | 11/1999 | Horiuchi et al. | 378/8 |
| 6,353,653 B1 | 3/2002 | Edic | |
| 6,370,217 B1 * | 4/2002 | Hu et al. | 378/8 |
| 6,535,570 B2 * | 3/2003 | Stergiopoulos et al. | 378/8 |
| 6,763,082 B2 * | 7/2004 | Ozaki | 378/8 |
| 6,775,346 B2 | 8/2004 | Heuscher et al. | |
| 7,382,852 B2 * | 6/2008 | Edic et al. | 378/8 |

(Continued)

FOREIGN PATENT DOCUMENTS

WO    9907283 A1    2/1999

OTHER PUBLICATIONS

Kak et al., Principles of computerized tomographic imaging, IEEE Pres, 1988, pp. 275-296.*

(Continued)

*Primary Examiner*—Edward J Glick
*Assistant Examiner*—Alexander H Taningco

(57) ABSTRACT

The invention relates to a method and a device for the iterative reconstruction of cross-sectional images of the heart (7) of a patient based on projections (P1, . . . P5) from different directions which are for example generated with a helical cone-beam CT scanner. A cardiac weight function (f) quantifies how near the projections (P1, . . . ) are to a given observation phase (To) of the heart cycle based on simultaneously recorded electrocardiographic signals (ECG). The whole set of projections (P1, . . . ) is divided into subsets (S1, . . . ) which each contain only projections corresponding to a similar cardiac weight (f), and an iterative reconstruction algorithm like ART uses in one update or iteration step all projections of such a subset (S1, . . . ) simultaneously.

20 Claims, 2 Drawing Sheets

U.S. PATENT DOCUMENTS

| | | | |
|---|---|---|---|
| 2002/0034276 A1* | 3/2002 | Hu et al. | 378/8 |
| 2003/0007593 A1* | 1/2003 | Heuscher et al. | 378/4 |
| 2004/0017881 A1* | 1/2004 | Cesmeli et al. | 378/4 |
| 2004/0131140 A1* | 7/2004 | Bruder et al. | 378/4 |

OTHER PUBLICATIONS

Carvalho, B. M. et al.; Helical CT Reconstruction from Wide Cone-Beam Angle Data using ART; 2003; Proc. XVI Brazilian Symposium on Computer Graphics and Image Processing; 8 pages.

Gordon, R., et al.; Algebraic Reconstruction Techniques (ART) for Three-dimensional Electron Microscopy and X-ray Photography; 1970; J. Theor. Biol.; 29:471-481.

Hudson, H. M., et al.; Accelerated Image Reconstruction Using Ordered Subsets of Projection Data; 1994; IEEE Trans. on Medical Imaging; 13(4)601-609.

Kachelriess, M., et al.; Image to Volume Weighting Generalized ASSR for Arbitrary Pitch 3D and Phase-Correlated 4D Spiral Cone-Beam CT Reconstruction; 2001; Proc. 6th Intl. Fully Three-Dimensional Image Reconstruction; pp. 179-182.

Lange, K., et al.; Globally Convergent Algorithms for Maximum a Posteriori Transmission Tomography; 1995; IEEE Trans. on Image Processing; 4(10)1430-1450.

Nielsen, T., et al.; Cardiac cone-beam CT volume reconstruction using ART; 2005; Med. Phys.; 32(4)851-860.

* cited by examiner

METHOD AND DEVICE FOR THE ITERATIVE RECONSTRUCTION OF CARDIAC IMAGES

FIELD OF THE INVENTION

The invention relates to a data processing unit, a method, an examination apparatus, and a record carrier for the iterative reconstruction of cross-sectional images of an object in a given phase of its cyclic movement, particularly in a given cardiac phase, using subsets of projections of the object.

BACKGROUND OF THE INVENTION

When a rotational X-ray device like a CT scanner generates X-ray projections of the heart during a rotation of the X-ray source, the resulting projections will capture the heart in different cardiac phases. Due to the associated movement of the heart, a tomographic reconstruction that simply uses all projections would yield a blurred cross-sectional image of the heart. It is therefore common to use for a reconstruction only projections that correspond (approximately) to the same cardiac phase, wherein the cardiac phase may for example be characterized by simultaneously recorded electrocardiographic signals. As was described in literature, this approach may for example be implemented based on a standard Algebraic Reconstruction Technique (ART) algorithm by the introduction of "cardiac weights" (cf. T. Nielsen, R. Manzke, R. Proksa, M. Grass: "Cardiac cone-beam CT volume reconstruction using ART", to be published in Med. Phys., 2005; T. Nielsen, et al.: "Feasibility Study of Iterative Reconstruction for Helical Cardiac Cone-Beam CT", scientific paper presented at RSNA 2004). Cardiac weights quantify with the help of electrocardiographic signals the similarity of a cardiac phase to a given observation phase that is of interest (for example the systolic phase or the diastolic phase).

To improve the speed of iterative reconstruction algorithms, it has further been proposed to divide all available projections randomly into subsets and to use in each iteration step all projections of a subset simultaneously for the calculation of an image update (resulting in the "Ordered Subsets" variants of the basic algorithms).

SUMMARY OF THE INVENTION

Based on this situation it was an object of the present invention to provide means for an improved iterative reconstruction of cross-sectional images of a cyclically moving object like the heart, particularly a reconstruction that is as fast as methods based on subsets while reducing image artifacts.

This object is achieved by a data processing unit according to claim 1, an examination apparatus according to claim 8, a method according to claim 9, and a record carrier according to claim 10. Preferred embodiments are disclosed in the dependent claims.

According to its first aspect, the invention relates to a data processing unit for the iterative reconstruction of cross-sectional images of a cyclically moving object in a user-given observation phase of the cyclic movement of the object. A typical example of such an object is the heart of a patient that moves periodically due to heart beat (and also due to respiration), but the invention is not restricted to this application. The data processing unit may basically be a computer with usual components like central processing unit, memory, I/O interfaces and the like together with appropriate software. It comprises the following modules which may be realized by dedicated hardware and/or software:

a) An input module for the reception of projections of the object that were generated from different directions and the reception of a simultaneously measured movement parameter, wherein said movement parameter characterizes the cyclic movement of the object at the time the associated projection was generated. The projections may particularly be X-ray projections of the object, and the movement parameter may particularly be an electrocardiographic signal characterizing the heart beat of a patient.

b) A sorting module for sorting projections received by the input module into subsets in such a way that all projections that were put into the same subset correspond to the same or to a similar phase of the cyclic movement of the object. All projections of one subset therefore have (approximately) the same similarity or distance to the given observation phase.

c) A reconstruction module for the iterative reconstruction of a cross-sectional image of the object with an iterative algorithm that processes in each iteration step all projections of at least one corresponding subset simultaneously (wherein the processed subset normally changes from iteration step to iteration step). In the iteration steps, projections are typically given less weight/influence with increasing distance to the observation phase.

The data processing unit described above allows a fast reconstruction of cross-sectional images of a cyclically moving object because it processes several projections in each iteration step simultaneously and because it takes the movement parameter of the projections into account. Moreover, the device achieves a high image quality with less artifacts compared to known approaches. This improvement is achieved by filling the subsets used in the iteration steps not randomly with projections but in an ordered fashion such that they comprise only projections of a similar movement phase.

According to a further development of the invention, the iterative reconstruction performed in the reconstruction module weights the processed projections with an aperture function. An aperture function simulates the effect that a real aperture or collimator would have on the measurements of a multi-pixel detector. It may particularly be applied in combination with projections generated by a multi-row detector which comprises an array with multiple rows and columns of detector units (pixels), wherein the signals generated by rows lying at the periphery of the array are preferably given less weight than those of central rows (cf. U.S. Pat. No. 6,775,346).

To facilitate the desired sorting of projections into subsets of similar-phase projections, the data processing unit preferably comprises a weighting module that is adapted to perform the step of associating weights to the movement parameters, wherein a weight measures the similarity of the movement parameter to the given observation phase. This similarity may for example be quantified by the temporal distance that the appearance of said movement parameter has from the appearance of the observation phase in one movement cycle of the object. In another approach, the similarity might be quantified by the difference of the considered parameter value to the parameter value of the observation phase. After association of weights to the movement parameters, subsets can readily be filled with projections having corresponding parameters with identical or similar weight. Moreover, the weights can be used in the iterations to quantify the influence of the projections.

The subsets generated by the sorting process are preferably of equal size such that each iteration step during the reconstruction processes approximately the same number of projections. The typical size of subsets depends on the pitch, the number of projections per rotation, and the total number of projections. The subsets are chosen in such a way, that each image value is illuminated in each subset by 5 to 1000 projections with cardiac weight>0, preferably by 15 to 200 projections.

In a typical case, the number of available projections that correspond to a certain movement phase is larger than the (desired) size of the subsets to be generated, and several subsets will therefore exist the projections of which all correspond to the same movement phase. In such a situation it is preferred to distribute the available projections of a certain movement phase randomly among the associated subsets.

A plurality of different iterative reconstruction algorithms has been described in literature. The iterative reconstruction applied hear may particularly be based on an Algebraic Reconstruction Technique (ART) (cf. R. Gordon, R. Bender, and G. T. Herman: "Algebraic reconstruction techniques (ART) for three-dimensional electron microscopy and x-ray photography", J. Theor. Biol., 29:471-481, 1970) or on a Maximum Likelihood (ML) algorithm (K. Lange and J. A. Fessler: "Globally convergent algorithms for maximum a posteriori transmission tomography", IEEE Transactions on Image Processing, 4(10):1430-1450, 1995), wherein each image update step uses the projections of a selected subset, i.e. projections corresponding to a similar movement phase.

The invention further relates to an examination apparatus, comprising the following components:

A rotational X-ray device for the generation of X-ray projections of an object from different directions. The X-ray device may particularly be a CT scanner, preferably a helical cone-beam CT scanner. In a helical cone-beam CT scanner, the X-ray source projects a cone beam on a corresponding detector and the source and at the detector make a helical movement relative to the examined object. This allows a fast acquisition of volume data and is therefore particularly suited for cardiac examinations.

An electrocardiographic device for measuring an electrocardiographic signal from a patient simultaneously to the generation of X-ray projections. With the electrocardiographic signal, the heart phase is known for each projection.

A data processing unit that is coupled to the X-ray device and to the electrocardiographic device and that is designed according to the principles of the data processing unit described above. Thus the data processing unit is particularly adapted to sort generated projections into subsets of similar movement phases and to reconstruct a cross-sectional image iteratively using projections of the subsets in the iteration steps.

The invention further comprises a method for the iterative reconstruction of cross-sectional images of an object in a given observation phase of its cyclic movement, wherein the reconstruction is based on projections of the object generated from different directions and on simultaneous measurements of a movement parameter that characterizes the cyclic movement of the object. The method comprises the following steps:

a) sorting of the projections into subsets such that the projections within each subset correspond to a similar phase of the cyclic movement; and b) iteratively reconstructing a cross-sectional image from the projections, wherein in each iteration step projections of at least one subset are processed simultaneously.

Finally, the invention comprises a record carrier, for example a floppy disk, a hard disk, or a compact disc (CD), on which a computer program for the iterative reconstruction of cross-sectional images of an object in a given observation phase of its cyclic movement is stored, said program being adapted to execute a method of the aforementioned kind.

The examination apparatus, the method, and the record carrier have similar features like a data processing unit that was described above. For more information on details, advantages and further developments of them reference is therefore made to the description of said unit.

These and other aspects of the invention will be apparent from and elucidated with reference to the embodiment(s) described hereinafter.

BRIEF DESCRIPTION OF THE DRAWINGS

In the following the invention is described by way of example with the help of the accompanying drawings in which.

DESCRIPTION OF PREFERRED EMBODIMENTS

Figure 1:
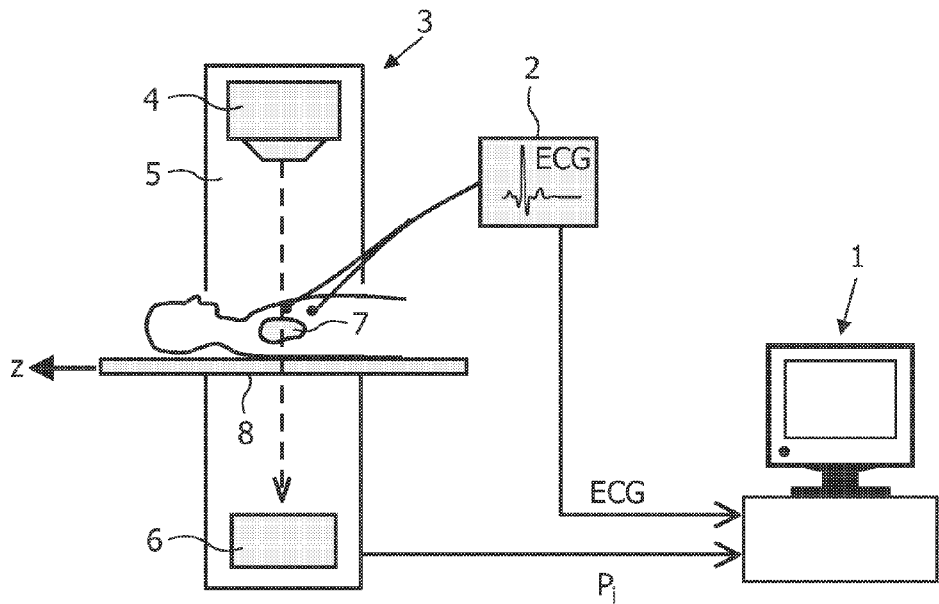
FIG. 1 schematically shows an examination apparatus for the reconstruction of cardiac images according to the present invention.

FIG. 1 schematically shows the main components of an examination apparatus according to the present invention. The apparatus comprises a rotational X-ray device 3 which is in this case particularly a helical cone-beam CT scanner. The CT scanner comprises in a gantry 5 an X-ray source 4 for the generation of a cone beam and a multi-row detector 6 opposite to the X-ray source 4. A patient on a table 8 is positioned with his heart 7 in the center of the gantry 5. The table 8 may be moved continuously in the direction z of the rotational axis such that a helical movement of the projection direction relative to the patient may be achieved.

The projections $P_i$ generated by the X-ray device 3 are communicated to a data processing unit or computer 1, where a cross-sectional image of the heart 7 shall be reconstructed.

FIG. 1 further shows an electrocardiographic device 2 that records via electrodes attached to the patient 7 electrocardiographic signals ECG and communicates them to the computer 1, where they are used as movement parameters characterizing the phase of the heart cycle.

Figure 2:
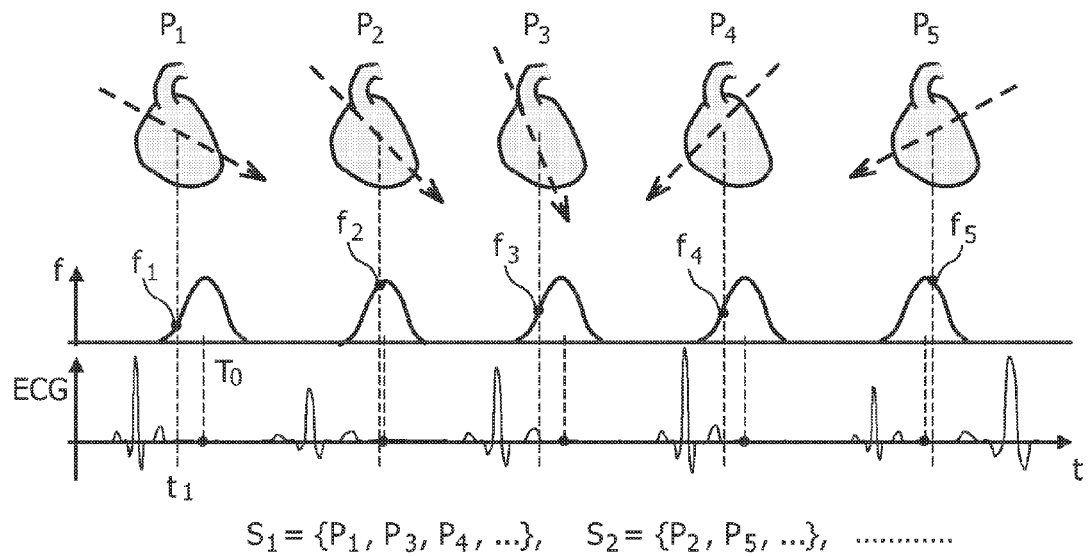
FIG. 2 schematically illustrates the iterative reconstruction method according to the present invention.

FIG. 2 shows schematically a series of projections $P_1, \ldots P_5$ generated from different directions during a rotation of the CT scanner 3 of FIG. 1. In the lower line of FIG. 2, the corresponding electrocardiographic signals ECG are depicted synchronously to the projections. Moreover, a cardiac weighting function f is shown in the middle of FIG. 2. The cardiac weighting function f consists of peaks having a predetermined width, wherein the peaks are centered at points $T_0, \ldots$ of each heart cycle corresponding to a user defined "observation phase". The peaks of the function f measure the distance (or the "similarity") that a considered cardiac phase, i.e. the time $t_i$ at which projection $P_i$ was generated, has with respect to the observation phase. Thus the function f can be used to weight the projections $P_1, \ldots$ by an associated factor $f_i = f(t_i)$ with respect to their distance to the observation phase (or, more exactly, with respect to the distance of their generation time $t_i$ to the observation phase). More details about the cardiac weights may be found in literature (cf. Nielsen et al., above).

The iterative reconstruction of helical cardiac scans with large area detectors may for example be performed with ART. If an acceleration of the reconstruction is desired by implementing the iterative algorithm on a dedicated hardware, the reconstruction has to be changed to "Simultaneous ART" (SART), which updates the image using several projections simultaneously. Another iterative algorithm which also requires a simultaneous processing of the projections is the Maximum Likelihood (ML) method. In particular, ML is preferred compared with ART, since it takes into account the photon statistics and achieves a better signal-to-noise ratio. In a variant of this algorithm called "Ordered Subset ML" (OSML), an update step uses not all projections but only a subset of them.

In a conventional "Convex OSML" algorithm (cf. K. Lange et al., above), the update for the j-th voxel $\mu_j^n$ in the n-th iteration step is for instance found to be $$\mu_j^{n+1} = \mu_j^n + \mu_j^n \frac{\sum_{i \in S_n} f_i A_{ij} \left[ d_i \exp\left(-\sum_v A_{iv}\mu_v^n\right) - Y_i \right]}{\sum_{i \in S_n} f_i A_{ij} \left(\sum_v A_{iv}\mu_v^n\right) \cdot d_i \exp\left(-\sum_v A_{iv}\mu_v^n\right)},$$

where $d_i$ and $Y_i$ are the emitted and observed numbers of photon counts, respectively, $A_{ij}$ are the components of the basis functions of the i-th projection, $f_i$ are the cardiac weights of the i-th projection, and $S_n$ describes the subset of projections used in the n-th iteration step (optionally aperture weights may be used to reduce artifacts, too).

An important point concerning iterative reconstruction is the selection of views (projections) for a subset $S_n$, which are processed simultaneously. It is known that a random selection of the views is easy to implement and achieves nearly the fastest speed of convergence for the iterative reconstruction. However, investigations showed that a random combination of all views for a cardiac weighted reconstruction leads to streaks which are visible in a sagittal view. This is due to the combination of projections $P_1, \ldots$ with different cardiac weighting factors $f_i$ in one subset.

In order to avoid the aforementioned problems, an optimal selection of projections for the subsets for iterative cardiac reconstruction is proposed here. The basic procedure of creating such optimal subsets $S_1, S_2, \ldots$ is the following:

1. Bin the projections $P_1, \ldots$ depending on their cardiac weight $f_1, \ldots f_5$.
2. Select a reasonable size of the subsets $S_1, S_2, \ldots$ to be generated.

A reasonable selection could be that all subsets are nearly equally filled.

3. Randomly fill the projections $P_1, \ldots$ from one bin (i.e. projections with a similar cardiac weight) in one or more subsets. In FIG. 2, the subset $S_2$ for example contains (only) projections $P_2, P_5, \ldots$ with a high cardiac weight.
4. Reconstruct the image with the generated subsets $S_1, S_2, \ldots$.

The described procedure ensures that the iterations converge smoothly. Without grouping the views with a similar cardiac weight, SART and ML are not be able to reconstruct a clinical relevant image.

Figure 3:
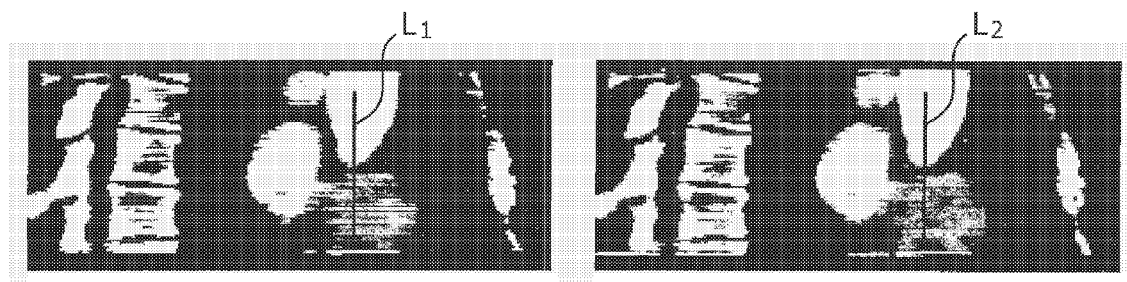
FIG. 3 shows an image of the heart reconstructed iteratively with a standard algorithm (OSML, left) and a method according to the present invention (right)

FIG. 3 shows a sagittal view (level 280/window 30) of a reconstructed heart after seven iterations with an iterative Ordered Subset Maximum Likelihood (OSML) algorithm using (a) a usual random selection of projections for the subsets (left picture) and (b) grouping the projections in subsets $S_1, S_2, \ldots$ depending on their cardiac weight (right picture).

Figure 4:
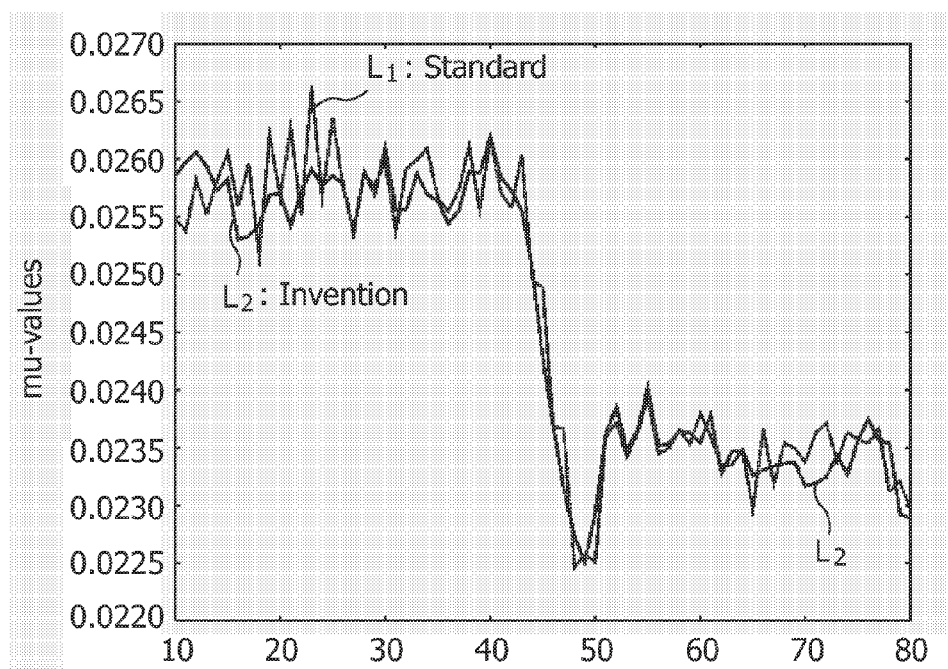
FIG. 4 shows a line-scan along the lines $L_1$, $L_2$ of FIG. 3.

FIG. 4 shows a line-scan along the lines $L_1$ and $L_2$ of FIG. 3, respectively. The curves reflect the smoother convergence of the optimal grouped subsets. For this reconstruction, the projections were binned in 10 bins depending on the cardiac weight. Subsets with a maximum size of 480 projections were created, where each subset has only views from one bin.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. A data processing unit for an iterative reconstruction of cross-sectional images of an object in a given observation phase of a cyclic movement of the object, comprising:
    an input module for reception of projections of the object from different directions and of simultaneously measured movement parameters characterizing the cyclic movement of the object;
    a processing module for determining a time distance from a projection to the observation phase for one or more of the projections;
    a sorting module for sorting the projections into subsets such that the projections within a subset correspond to a predetermined time distance range to the observation phase; and
    a reconstruction module for the iterative reconstruction of a cross-sectional image with an algorithm that processes in each iteration all projections of at least one subset.

2. The data processing unit according to claim 1, wherein the iterative reconstruction weights projections with an aperture function.

3. The data processing unit according to claim 1, wherein the projections are X-ray projections.

4. The data processing unit according to claim 1, further including a weighting module for associating a weight to the movement parameters that measures the similarity of the movement parameters to the observation phase.

5. The data processing unit according to claim 1, wherein the subsets are approximately of equal size.

6. The data processing unit according to claim 1, wherein projections corresponding to similar time distance ranges are distributed randomly among the associated subsets.

7. The data processing unit according to claim 1, wherein the iterative reconstruction is based on an ART or ML algorithm, wherein an image update in each iteration uses all projections of a selected subset.

8. The data processing unit according to claim 1, wherein the projections are weighted with a weight to determine the time distance.

9. The data processing unit according to claim 8, wherein the weighting is applied to the projections with a weighting function.

10. The data processing unit according to claim 9, wherein the weighting function is variable and includes a peak of a predetermined width centered at the observation phase.

11. An examination apparatus, comprising
a rotational X-ray device;
an electrocardiographic device; and
a data processing unit according to claim 1 that is coupled to the X-ray device and the electrocardiographic device.

12. A method for the iterative reconstruction of cross-sectional images of an object in a given observation phase of a cyclic movement of the object based on projections of the object from different directions and on simultaneous measurements of movement parameters characterizing the associated cyclic movement of the object, comprising:
determining a time distance from a projection to the observation base for one or more of the projections;
sorting the projections into subsets such that the projections within a subset correspond to a redetermined time distance range to the observation phase; and
iteratively reconstructing a cross-sectional image from the projections, wherein in an iteration all projections of at least one subset are processed.

13. A computer readable medium on which a computer program for the iterative reconstruction of cross-sectional images of the object in the given observation phase of its cyclic movement is stored, said computer program being adapted to execute the method according to claim 12.

14. The method according to claim 12, wherein the iterative reconstruction further includes weighting projections with an aperture function.

15. The method according to claim 12, further including applying a weighting to the projections to determine the time distance.

16. The method according to claim 15, further including applying the weighting to the projections with a weighting function.

17. The method according to claim 16, wherein the weighting function is variable and includes a peak of a predetermined width centered at the observation phase.

18. The method according to claim 12, further including weighting the movement parameters with a weighting module that measures the similarity of the movement parameters to the observation phase.

19. The method according to claim 12, further including sorting the subsets such that the subsets are filled with approximately a same number of projections.

20. The method according to claim 12, further including distributing projections corresponding to similar time distance ranges randomly among the associated subsets.

* * * * *